United States Patent [19]

Graham

[11] Patent Number: 4,597,777
[45] Date of Patent: Jul. 1, 1986

[54] MEMBRANE GAS SEPARATION PROCESSES

[75] Inventor: Tommy E. Graham, Raleigh, N.C.

[73] Assignee: Monsanto Company, St. Louis, Mo.

[21] Appl. No.: 466,686

[22] Filed: Feb. 15, 1983

[51] Int. Cl.[4] ............................................. B01D 53/22
[52] U.S. Cl. .......................................... 55/16; 55/68; 55/158
[58] Field of Search ............................... 55/16, 68, 158

[56] References Cited

U.S. PATENT DOCUMENTS

| | | | |
|---|---|---|---|
| 3,534,528 | 10/1970 | Porter | 55/16 |
| 3,713,271 | 1/1973 | Franz et al. | 55/16 |
| 4,130,403 | 12/1978 | Cooley et al. | 55/68 X |
| 4,264,338 | 4/1981 | Null | 55/16 |
| 4,364,759 | 12/1982 | Brooks et al. | 55/16 X |
| 4,370,150 | 1/1982 | Fenstermaker | 55/16 |
| 4,374,657 | 2/1983 | Schendel et al. | 55/16 X |

Primary Examiner—Robert Spitzer
Attorney, Agent, or Firm—H. Croskell

[57] ABSTRACT

This invention relates to membrane gas separation of carbon dioxide and methane containing gas mixtures. More particularly the invention relates to apparatus and processes for recovering a methane-enriched non-permeate gas of natural gas pipe line quality from mixtures of carbon dioxide and methane where membrane permeate gases contain substantially all of the carbon dioxide of the feed gas mixture. An aspect of the process of this invention is that a significant portion of the carbon dioxide containing permeate gas can be utilized as combustion engine fuel to drive feed gas compressors utilized in the process.

9 Claims, 4 Drawing Figures

4,597,777

MEMBRANE GAS SEPARATION PROCESSES

BACKGROUND OF THE INVENTION

The field of this invention is membrane gas separation apparatus and processes for recovering a methane-enriched gas from a mixture comprising methane and carbon dioxide.

To date a number of membrane gas separation processes have found commercial acceptance because of the compatability of specific membrane gas separation operations in the economic feasibility of operating such processes. Such processes include the recovery of hydrogen from purge gas streams, for instance from ammonia production processes or from hydrogen treating processes. In some instances separation of carbon dioxide and methane by membrane permeation is also economically feasible depending on the value of gases recovered in those operations in particular industries. One source of gas mixtures of carbon dioxide and methane is sanitary landfill wells which recover gas mixtures which are generated by the decomposition of solid waste in sanitary landfills; other sources include plant and/or animal waste digesters, including sewerage treatment plants and the like.

Such gases, for instance from sanitary landfills, are usually available at a well head pressure of less than about 2 atmospheres. Separation of such gases to natural gas pipe line quality methane by a membrane gas separation process usually requires compression of the well head gas mixture from such low pressure for instance, about atmospheric pressure, to substantially high pressure, for instance greater than about 100 psia. Depending on the membrane utilized and its permeation characteristics, it may be desirable to compress such low pressure gas mixture up to as high as 600 psia or even higher. The costs of compression often are substantially high and in some instances may preclude the economic feasibility of a membrane gas separation to recover methane from gases generated by sanitary landfills, digesters and the like. What has been discovered is an effective process and apparatus for recovering methane as a non-permeating gas by membrane gas separators, where substantial quantities of a carbon dioxide-containing permeate gas can be utilized as combustion fuel to provide power for compression of feed gas mixtures to be separated.

In describing the present invention a particularly convenient analytical characteristic of polymeric gas permeable membranes includes the permeability of the membrane for a specific gas through the membrane. The permeability ($P_a/l$) of a membrane for gas "a" of a gas mixture through a membrane of thickness "l" is the volume of gas, referred to standard temperature and pressure (STP), which passes through the membrane per unit of surface area of membrane, per unit of time, per unit of differential partial pressure of the permeating species across the thickness of the membrane. One method for expressing permeabilities is cubic centimeters (STP) per square centimeter of membrane area per second per differential partial pressure of 1 centimeter of mercury across the membrane thickness ($cm^3(STP)/cm^2$-sec-cmHg). Unless otherwise noted, all permeabilities are reported herein at standard temperatures and pressures of 60° F. and 14.7 psia, respectively. Permeabilities are generally reported in gas permeation units (GPU), which are $cm^3(STP)$ $cm^2$-sec-cmHg$\times 10^6$; thus 1 GPU is $1\times 10^{-6} cm^3(STP)$ $cm^2$-sec cmHg. Another convenient relationship for expressing gas permeation characteristics of membranes is separation factor. A separation factor, $\alpha$ a/b, for a membrane for a given pair of gases "a" and "b" is defined as the ratio of the permeability ($P_a/l$) of a membrane of thickness "l" for a gas "a" of a gas mixture to the permeability ($P_b/l$) of the same membrane to gas "b".

In practice, separation factor with respect to a given pair of gases for a given membrane can be determined by employing numerous techniques which provide sufficient information for calculation of permeabilities for each of the gases. Several of the many techniques available for determining permeabilities and separation factors are disclosed by Hwang et.al., *Techniques of Chemistry*, Volume VII, Membranes in Separations John Wiley & Sons, 1974 (herein incorporated by reference), at Chapter XII, pages 296-322.

Measurements can be made for pure gas permeation or for blend gas permeation. However, experience has shown that the measured permeability of a membrane for a gas species is higher for pure gas permeation than for blend gas permeation. In general, it is more desirable to determine gas permeation characteristics for blend gases, since the permeabilities and separation factors more closely predict actual membrane gas separation performance characteristics.

When a plurality of membranes are assembled into a separator in modular form, it is generally convenient to establish some standard sizes for such modularized membrane gas separators in terms of the amount of membrane surface area. For instance, one standard separator could have 150 square meters of membrane surface area while another standard separator could have 10,000 square meters of membrane surface area. When dealing with modularized membrane gas separators a convenient way of characterizing the permeation performance of a standard membrane gas separator is in terms of modular permeability which is the product of membrane surface area (A) and permeability (P/l). Unless otherwise stated modular permeability is expressed in modular flow units (MFU) which are $cm^3(STP)$/sec-cmHg. For instance a separator having a membrane surface area of 1000 square meters ($10^7 cm^2$) where the membrane exhibits a permeability for gas "a" of 25.0 GPU (that is, $25\times 10^{-6} cm^3(STP)$ $cm^2$-sec-cmHg), exhibit a modular permeability for gas "a" of 250 MFU.

SUMMARY OF THE INVENTION

This invention provides a membrane gas separator apparatus for recovering a methane-enriched non-permeate gas from a mixture comprising methane and carbon dioxide. The apparatus comprises at least one first separator having a membrane exhibiting selectivity to the permeation of carbon dioxide; at least one subsequent separator having a membrane exhibiting selectivity to the permeation of carbon dioxide; a combustion engine for generating power; means for providing said mixture at a permeating pressure to said at least one first separator; means for conducting a non-permeate gas from said at least one first separator to said at least one subsequent separator; means for withdrawing carbon dioxide-enriched permeate gas from said at least one first separator; means for withdrawing a methane-enriched non-permeate gas from said at least one subsequent separator; means for conducting a combustible permeate gas from said at least one subsequent separator to a fuel inlet of said combustion engine; and means for transmitting power from said combustion engine to said means for providing said mixture at a permeating pressure. The apparatus may further comprise a manifold having at least one connection to said means for withdrawing a carbon dioxide-enriched permeate gas from said at least one first separator and at least one connection to said means for conducting a combustible permeate gas from said at least one subsequent separator.

The apparatus may comprise as few as two separators, one being a first separator and the other being a subsequent separator. More often, the apparatus will comprise more than one first separator and more than one subsequent separator. For instance, the appartaus may comprise up to ten or even more separators, some of which will be first separators and others of which will be subsequent separators, depending on the nature and disposition of the permeate gas from any one of such separator.

In another aspect of this invention, the apparatus will further comprise valves in said manifold between said connections. It is often desirable that there be means for operating said valves responsive to a fuel requirement of said combustion engine. In the operation of this apparatus, said valves can be manipulated to divert a combustible permeate gas from said subsequent separators to a fuel inlet of said combustion engine depending on the fuel valve of the permeate gas.

This invention also provides a membrane gas separation process for recovering a methane-enriched non-permeate gas from a mixture comprising methane and carbon dioxide. This process comprises passing said mixture to a means for providing said mixture at a permeating pressure, passing said mixture at a permeating pressure to at least one first separator having a membrane exhibiting selectivity to the permeation of carbon dioxide, allowing the non-permeate gas from said at least one first separator to pass at a permeating pressure to at least one subsequent separator having a membrane exhibiting selectivity to the permeation of carbon dioxide, withdrawing a carbon dioxide-enriched permeate gas from said at least one first separator, withdrawing a methane-enriched non-permeate gas from said at least one subsequent separator, and withdrawing a combustible permeate gas from said at least one subsequent separator.

The process of this invention is advantageous and useful in recovering a methane-enriched non-permeate gas from a mixture comprising from about 30 to about 60 mole percent carbon dioxide and from about 30 to about 80 mole percent methane. Depending on the source, such gas mixtures may also comprise substantial quantities of nitrogen, say up to 20 mole percent nitrogen. Other gases, including water vapor, oxygen, hydrogen sulfide, ammonia, mercaptans, and the like may be present, usually in small quantities, depending on the source of the mixture. The process is particularly advantageous where said combustible permeate gas mixture withdrawn from said at least one subsequent separator comprises at least about 40 mole percent methane.

In the process of this invention, it is also desirable that the membrane of said at least one first separator and the membrane of said at least one subsequent separator exhibit a selectivity for permeation of carbon dioxide to the permeation of methane to at least about 9 to 1.

In Order to utilize the recovered methane-enriched non-permeate gas, it is often desired that the process be operated such that the methane-enriched non-permeate gas comprises at least 80 mole percent methane. In some cases, at least 90 mole percent methane is desired, and in other cases, 95 mole percent methane or higher is required. Regardless of the composition requirement for the methane-enriched non-permeate gas, it is generally desired that the methane-enriched non-permeate gas will comprise, that is recover, at least 60 percent of the total methane in the mixture which is passed at a permeating pressure to at least one first separator.

The process of this invention has particular economic advantages when the combustible permeate gas from said at least one subsequent separator is used as fuel to a combustion engine which can generate power to drive said means for providing said gas mixture at a permeating pressure. This can be achieved when the means for providing said mixture at a permeating pressure is driven by direct mechanical power coupling to a combustion engine fueled by said combustible permeate gas. Alternatively, the combustible gas can be used as fuel for a combustion engine-driven electric power generator which provides electric power for driving an electric motor-driven means for providing said mixture at a permeating pressure. In some cases, it may be desirable to export such generated electric power, for instance, to a utility in exchange for credit for electric power used to drive equipment which may be utilized in the process of this invention. In some cases, it may be necessary or even desirable to mix a portion of said methane-enriched non-permeate gas to said combustible permeate gas depending on combustible gas conditions and flow rates.

DESCRIPTION OF THE PREFERRED EMBODIMENTS

Figure 1:
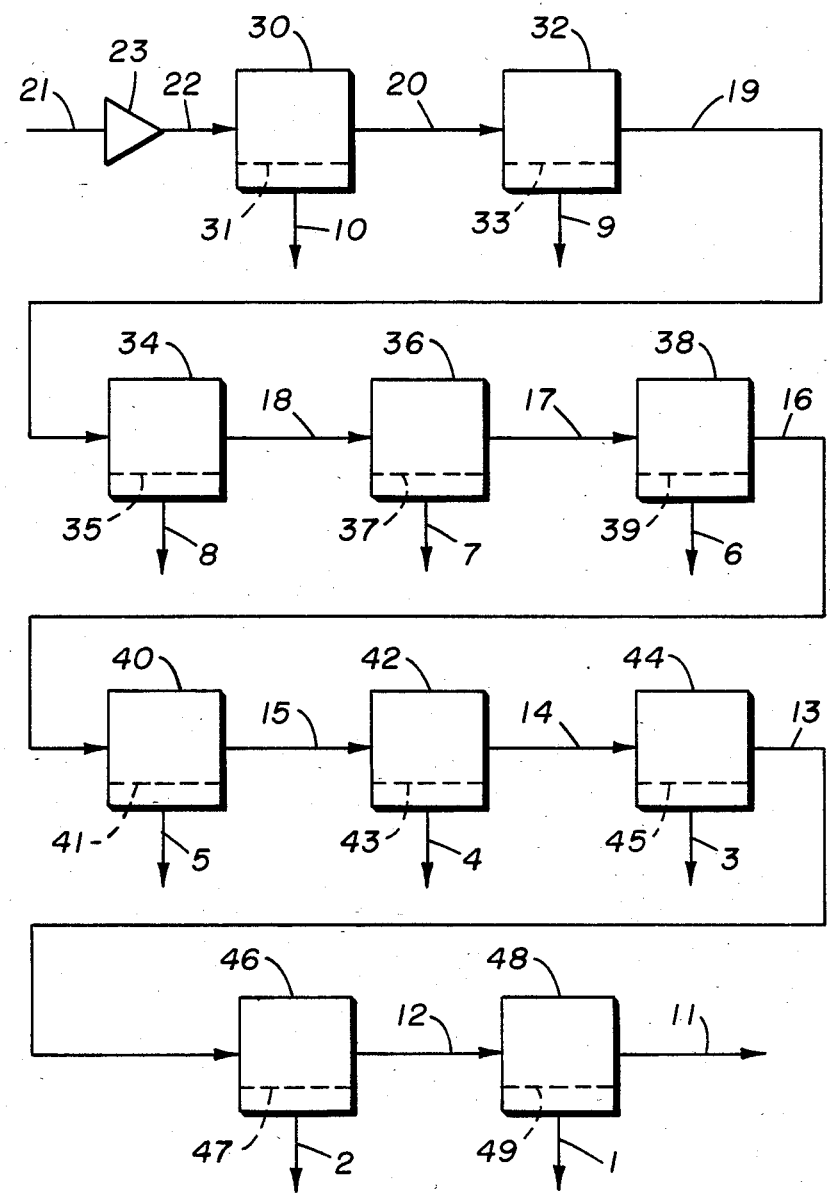
FIGS. 1, 2 and 3 are schematic representaiton of apparatus of the present invention, and apparatus which may be utilized to carry out aspects of the process of the present invention.

Referring now in detail to the drawings, FIG. 1 schematically illustrates an apparatus embodying an aspect of the present invention and useful for carrying out an aspect of the process of the present invention. A feed gas comprising a hydrocarbon gas, such as methane, and an acid gas, such as carbon dioxide, is fed through a line 21 to a means for providing the mixture at a permeating pressure, for instance a compressor 23. The mixture at a permeating pressure is fed through line 22 to a series of ten separators 30, 32, 34, 36, 38, 40, 42, 44, 46 and 48. Each separator has a membrane 31, 33, 35, 37, 39, 41, 43, 45, 47 and 49. Each membrane exhibits a selectivity to the permeation of carbon dioxide as compared to the permeation of methane.

The non-permeating gas passes with little pressure drop in its permeating pressure between the separators through lines 20, 19, 18, 17, 16, 15, 14, 13 and 12 with a progressively increasing enrichment in methane until the non-permeate gas finally is withdrawn from separator 48 through line 11 substantially increased in methane to a desired level, for instance at least about 90 mole percent or higher, say 93 mole percent or even 95 mole percent.

A permeating gas substantially enriched in carbon dioxide as compared to the gas supplied to a separator is withdrawn from each of the ten separators through a separate line, for instance through line of lines 10, 9, 8, 7, 6, 5, 4, 3, 2 and 1. The composition of the permeating gas withdrawn from each successive separator is decreasingly reduced in carbon dioxide concentration. For instance, the permeate gas withdrawn through line 10 will have the highest concentration of carbon dioxide; and the permeate gas withdrawn through line 1 will have the lowest concentration of carbon dioxide. As the concentration of carbon dioxide is progressively reduced, the concentration of methane in the permeating gas will be progressively increased.

Depending upon the total feed gas flow rate and composition, as well as gas pressures on opposing sides of the membranes, the concentration of carbon dioxide and methane in the permeating gas will vary for a given system. In some cases, the permeating gas withdrawn from the first separator, for instance the gas withdrawn from separator 30 through line 10, will be sufficiently high in carbon dioxide concentration and, likewise, sufficiently low in methane concentration to be of no value as a combustible fuel. For instance, this permeating gas stream may have a heating value of about 200 British Thermal Units per standard cubic foot (BTU/SCF). This is equivalent to 7450 kilojoules per cubic meter ($kJ/m^3$). The permeating gas stream may have even lower heating values, say 150 BTU/SCF (5590 $kJ/m^3$) or even 100 BTU/SCF (3726 $kJ/m^3$). On the hand, the stream permeating in separator 48 and withdrawn through line 1 will generally have a much higher concentration of methane and may even generally comprise substantial quantities of methane, for instance, in the range of 60 to 80 mole percent methane and have a heating value of greater than about 600 BTU/SCF (22,360 $kJ/m^3$).

The compositions of the permeating gases from intermediate separators will fall within a progressive range between the limits established by the compositions of the first and last separators. In general, several of the permeating gas streams from the downstream separators, say for instance, separators 42, 44, 46 and 48, can be combined to provide a combustible fuel gas stream having a heating value suitable for use as fuel in a combustion engine. As gas compositions for fuel requirements may change depending on process conditions, for instance feed gas composition, more or less of the permeating feed gas streams can be combined to form the combustible fuel gas stream. Such combustible fuel gas can be used in a combustion engine to generate power which can be utilized by the means for providing the mixture at a permeating pressure, for instance compressor 23.

Figure 2:
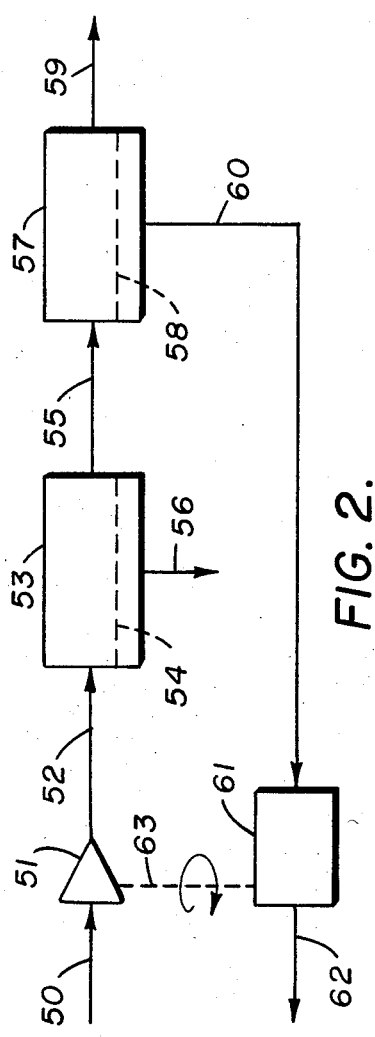

Referring now to FIG. 2, there is shown a schematic representation of alternative apparatus for carrying out an aspect of the present invention. A feed gas mixture comprising, for instance, methane and carbon dioxide is supplied through line 50 to a compressor 51 which serves as means for providing said mixture at a permeating pressure. The gas mixture at a permeating pressure is provided to the separator 53 through line 52. Separator 53 has a membrane 54 which exhibits selectivity to the permeation of carbon dioxide. A permeating gas substantially enriched in carbon dioxide is withdrawn from separator 53 through line 56. A non-permeating gas enriched in methane is withdrawn from separator 53 and passed to separator 57 through line 55.

Separator 57 has a membrane 58 which exhibits a selectivity to the permeation of carbon dioxide. A non-permeating gas substantially enriched in methane, for instance to the level of about 90 mole percent methane or higher, is withdrawn through line 59. A permeating gas enriched in carbon dioxide as compared to the gas fed to separator 57 through line 55 is withdrawn from separator 57 through line 60. Since such gas, as is in line 60, will also comprise a significant amount of methane, for instance to have a heating value of at least about 400 BTU/SCF (14,000 $kJ/m^3$), it can be fed to a combustion engine 61. Exhaust gases from the combustion engine 61 are vented through line 62. Power generated by the combustion engine 61 is transmitted to the compressor 51 by the means for transmitting power 63.

Figure 3:
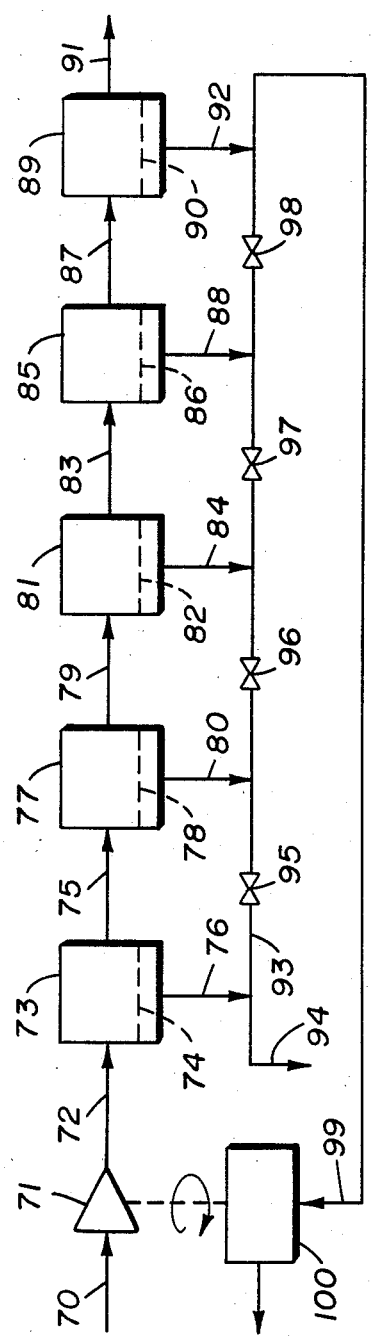

Referring now to FIG. 3 there is shown apparatus embodying an alternative aspect of the present invention. The feed gas mixture comprising, for instance, methane and carbon dioxide, is supplied through line 70 to a means for providing said mixture at a permeating pressure, such as compressor 71. The gas mixture at a permeating pressure is provided to a series of five separators 73, 77, 81, 85 and 89 each of which has a membrane 74, 78, 82, 86 and 90, respectively, which membrane exhibits selectivity to the permeation of carbon dioxide.

The non-permeating gas passes between separators with increasing enrichment in methane through lines 75, 79, 83 and 87 and finally exits separator 89 through line 91 being significantly enriched in methane, for instance to a level of about 90 mole percent methane or higher.

Permeating gas is withdrawn from the separators through lines 76, 80, 84, 88 and 92. Among these permeating gas streams, the permeating gas withdrawn from separator 73 through line 76 will have the highest concentration of carbon dioxide and the permeating gas withdrawn from permeator 89 through line 92 will have the highest concentration of methane.

The permeate gas streams are connected to a manifold 93 with valves 95, 96, 97 and 98 located in the manifold between connections to the manifold by the lines withdrawing gas from the separators. Depending on the feed gas composition flow rate and permeator performance the composition of the permeate gas streams will vary. In general the permeating gas streams will exhibit a progressively increasing level of methane from line 76 through lines 80, 84 and 88 to line 92. By operation of any one of valves 95, 96, 97 or 98, the permeating gas in the manifold can be diverted into two streams. The low heating value gas comprising mostly carbon dioxide can be vented, for instance through line 94. The high heating value gas comprising substantial amounts of methane can be routed through line 99 to a combustion engine 100 which generates power to operate compressor 71 which serves as means for providing the gas mixture at permeating pressure.

As a result of extensive membrane gas separation operations, a considerable body of membrane permeation data has been accumulated which assures that computer assisted simulations of membrane gas separations can be utilized to predict membrane gas separator performance with reasonable accuracy. The following example is based on the computer simulation of a membrane separation of a gas mixture comprising carbon dioxide and methane. This example illustrates the process of recovering a methane-enriched non-permeate gas from the mixture comprising methane and carbon dioxide where a portion of the permeating gas from a portion of the separator has a sufficiently high heating value to be utilized as fuel for a combustion engine.

EXAMPLE I

A computer simulation of a membrane gas separation is illustrated in this example utilizing a feed gas comprising 43.88 mole percent carbon dioxide, 55.35 mole percent methane, 0.40 mole percent nitrogen, 0.10 mole percent oxygen and 0.27 mole percent water. Such feed gas is provided at a flow rate of 41,600 standard cubic feet per hour (SCFH, as measured at 60° F. and 14.7 psia). This is equivalent to a flow rate of 1115 normal cubic meters per hour ($Nm^3/hr$). The feed gas is provided at a permeating pressure of 400 psia. This is equivalent to a pressure of 275 kilo pascal (kPa). The feed gas is supplied to a series of ten separators, each having a membrane exhibiting selectivity to the permeation of carbon dioxide. The separator arrangement is as illustrated in FIG. 1.

Each separator has the same amount of membrane surface area and is characterized as having a modular permeability for carbon dioxide of 44 MFU (as defined above) and a modular permeability for methane of 3.0 MFU. Based on the modular permeabilities for carbon dioxide and methane, the membrane exhibits a selectivity to the permeation of carbon dioxide compared to the permeation of methane of 14, that is the membrane has a separation factor, designated as $\alpha(CO_2/CH_4)$, of 14. The separators are each operated such that the permeating gas pressure is maintained at 25 psia (172 kPa). Table 1 summarizes compositions and flow rates for non-permeate and permeate gas streams where the stream numbers correspond to the streams in lines designated by the same number in FIG. 1.

Further reference to Table 1 shows that stream 1, which designates the permeate gas from the last separator in the series, will comprise 70.33 mole percent methane and 29.06 mole percent carbon dioxide. This permeate gas will be at a total flow rate of 1,100 SCFH (29 $Nm^3/hr$). This gas stream can be provided to a combustion engine to provide 85 horsepower (hr), which is equivalent to 63 killowatt (kw).

Figure 4:
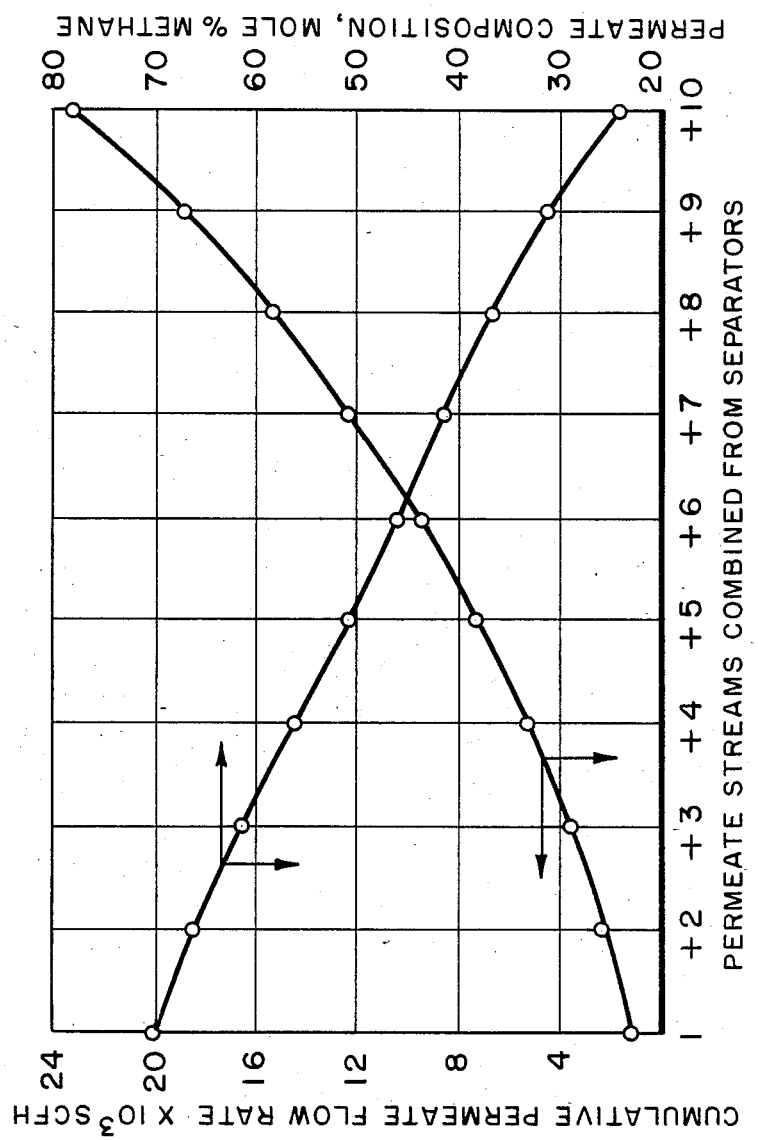
FIG. 4 is a graphical illustration of comulative permeate gas flow rate and composition as permeate gas streams are combined.

The permeate gas from other separators can be combined. Preferably, such combined permeate streams will be those having the next highest level of methane. FIG. 4 illustrates the cumulative effects of combining additional permeate gas streams with stream 1. As can be expected as the total cumulative permeate gas flow increases, the overall methane composition in the combined permeate gas will decrease. The cumulative permeate gas flows are summarized in Table 2 which also shows the total available combustion engine horsepower from the combined permeate gas streams. It is preferred to avoid combining permeate gas streams such that the methane composition falls below about 60 mole percent methane. However, in some cases, it is possible to achieve reasonable combustion operations with gas streams having between about 40 and about 60 mole percent methane. Generally, it is undesirable to combine permeate gas streams such that the methane composition of the cumulative permeate gas stream to be used as combustion engine fuel falls below 40 mole percent methane.

In Example I, the compression requirement to raise the total feed gas stream of 41,600 SCFH (1115 $Nm^3/hr$) from 25 psia (172 kPa) to 400 psia (2758 kPa) is approximately 225 brake horsepower (168 kw). It can be seen from available combustion engine horsepower indicated in Table 2 that it would be necessary only to combine the permeate streams from the last three separators for use as combustion engine fuel to provide sufficient horsepower to operate the membrane gas separation process illustrated in Example I.

TABLE 1

| PERMEATOR GAS STREAMS | | | | | | | | | | |
|---|---|---|---|---|---|---|---|---|---|---|
| Stream No. | 20 | 19 | 18 | 17 | 16 | 15 | 14 | 13 | 12 | 11 |
| Non-Permeate | | | | | | | | | | |
| Composition (mole percent): | | | | | | | | | | |
| $CO_2$ | 38.65 | 33.20 | 27.74 | 22.53 | 17.82 | 13.76 | 20.40 | 7.73 | 5.75 | 4.06 |
| $CH_4$ | 60.66 | 66.14 | 71.59 | 76.77 | 81.45 | 85.49 | 88.82 | 91.47 | 93.53 | 95.10 |
| $N_2$ | .44 | .48 | .53 | .57 | .61 | .64 | .67 | .70 | .72 | .75 |
| $O_2$ | .11 | .11 | .11 | .11 | .11 | .11 | .11 | .10 | .10 | .09 |
| $H_2O$ | .14 | .07 | .03 | .02 | .01 | .00 | .00 | .00 | .00 | .00 |
| Flow Rate: | | | | | | | | | | |
| $10^3$ SCFH | 35.8 | 32.0 | 28.8 | 26.0 | 23.7 | 21.8 | 20.1 | 18.7 | 17.5 | 16.4 |
| ($Nm^3/hr$) | (960) | (858) | (772) | (697) | (635) | (584) | (539) | (501) | (469) | (440) |
| Stream No. | 10 | 9 | 8 | 7 | 6 | 5 | 4 | 3 | 2 | 1 |
| Permeate | | | | | | | | | | |
| Composition (mole percent): | | | | | | | | | | |
| $CO_2$ | 87.12 | 84.79 | 81.39 | 76.73 | 70.70 | 63.33 | 54.92 | 45.99 | 37.18 | 29.06 |
| $CH_4$ | 11.43 | 14.31 | 18.02 | 22.83 | 28.92 | 36.27 | 44.64 | 53.52 | 62.26 | 70.33 |
| $N_2$ | .06 | .08 | .10 | .13 | .16 | .21 | .26 | .31 | .37 | .42 |
| $O_2$ | .06 | .07 | .08 | .10 | .11 | .14 | .15 | .17 | .18 | .19 |
| $H_2O$ | 1.32 | .75 | .41 | .21 | .11 | .05 | .03 | .01 | .01 | .00 |
| Flow Rate: | | | | | | | | | | |
| $10^3$ SCFH | 4.3 | 3.8 | 3.2 | 2.8 | 2.3 | | | | | |
| ($Nm^3/hr$) | (115) | (102) | (86) | (75) | (62) | (51) | (46) | (38) | (32) | (29) |

Stream No. corresponds to streams in lines designated by same number in FIG. 1. Compositions are given in mole percent.

As shown in Table 1, stream 11, which designates the non-permeate gas from the last separator in the series, comprises 95.1 mole percent methane and 4.06 mole percent carbon dioxide. This non-permeate gas will be at a total flow rate of 16,400 SCFH (440 $Nm^3/hr$). The methane in this non-permeate gas comprises 70 percent of the total methane in the feed gas.

TABLE 2

| COMBINED PER-MEATE STREAMS | PERMEATE GAS STREAM ADDITION ||||||
|---|---|---|---|---|---|---|
| | CUMULATIVE FLOW RATE || METHANE COMPOSITION | CUMULATIVE METHANE FLOW || AVAILABLE COMBUSTION ENGINE POWER ||
| | 10³ SCFH | (Nm³/hr) | mole percent | 10³ SCFH | (Nm³/hr) | HP | (KW) |
| 1 | 1.1 | (29) | 70 | 0.77 | (21) | 85 | (63) |
| +2 | 2.3 | (61) | 66 | 1.52 | (41) | 170 | (127) |
| +3 | 3.7 | (99) | 61 | 2.27 | (61) | 250 | (186) |
| +4 | 5.4 | (145) | 56 | 3.03 | (81) | 337 | (251) |
| +5 | 7.3 | (196) | 51 | 3.72 | (100) | 370 | (276) |
| +6 | 9.6 | (258) | 46 | 4.38 | (117) | 440 | (328) |
| +7 | 12.4 | (333) | 41 | 5.08 | (136) | 510 | (380) |
| +8 | 15.6 | (419) | 36 | — | | — | |
| +9 | 19.4 | (521) | 32 | — | | — | |
| +10 | 23.7 | (636) | 24 | — | | — | |

What is claimed is:

1. A membrane gas separator apparatus for recovering a methane-enriched non-permeate gas from a mixture comprising methane and carbon dioxide, said appartaus comprising at least one first separator having a membrane exhibiting selectivity to the permeation of carbon dioxide; at least one subsequent separator having a membrane exhibiting selectivity to the permeation of carbon dioxide; a combustion engine for generating power; means for providing said mixture at a permeating pressure to said at least one first separator; means for conducting a non-permeate gas from said at least one first separator to said at least one subsequent separator; means for withdrawing carbon dioxide-enriched permeate gas from said at least one first separator; means for withdrawing a methane-enriched non-permeate gas from said at least one subsequent separator; means for conducting a combustible permeate gas from said at least one subsequent separator to a fuel inlet of said combustion engine; and means for transmitting power from said combustion engine to said means for providing said mixture at a permeating pressure.

2. The separator of claim 1 further comprising a manifold having at least one connection to said means for withdrawing a carbon dioxide-enriched permeate gas from said at least one first separator and at least one connection to said means for conducting a combustible permeate gas from said at least one subsequent separator.

3. The separator of claim 2 having valves in said manifold between said connections.

4. The separator of claim 3 further comprising means for operating said valves responsive to a fuel requirement of said combustion engine-driven means.

5. A membrane gas separation process for recovering from a mixture comprising from 30 to 70 mole percent methane and from 30 to 60 mole percent carbon dioxide a methane-enriched non-permeate gas said process comprising (a) passing said mixture to means for providing said mixture at a permeating pressure;

(b) passing said mixture at a permeating pressure to at least one first separator having a membrane exhibiting selectivity to the permeation of carbon dioxide, wherein the separation factor, $\alpha CO_2/CH_4$, is at least about 9;

(c) allowing the non-permeate gas from said at least one first separator to pass at a permeating pressure to at least one subsequent separator having a membrane exhibiting selectivity to the permeation of carbon dioxide, wherein the separation factor, $\alpha CO_2/CH_4$, is at least about 9;

(d) withdrawing a carbon dioxide-enriched permeate gas from said at least one first separator;

(e) withdrawing a methane-enriched non-permeate gas comprising at least about 90 mole percent methane from said at least one subsequent separator; and (f) allowing a combustible permeate gas comprising at least about 40 mole percent methane to flow from said at least one subsequent separator to a combustion engine having means to transmit power to said means for providing said mixture at a permeating pressure.

6. The process of claim 5 wherein said methane-enriched non-permeate gas comprises at least 60 percent of the total methane in said mixture.

7. The process of claim 6 wherein power is mechanically transmitted from said combustion engine to said means for providing said mixture at a permeating pressure.

8. The process of claim 6 wherein said means for providing said mixture at a permeating pressure is driven by electric power and said combustible permeate gas is used as fuel for a combustion engine-driven electric power generator.

9. The process of claim 6 wherein a portion of said methane-enriched non-permeate gas is added to said combustible permeate gas.

* * * * *